(12) United States Patent
Shi et al.

(10) Patent No.: US 10,304,180 B2
(45) Date of Patent: *May 28, 2019

(54) APPARATUS AND METHODS FOR PREDICTING WAFER-LEVEL DEFECT PRINTABILITY

(71) Applicant: KLA-Tencor Corporation, Milpitas, CA (US)

(72) Inventors: Rui-fang Shi, Cupertino, CA (US); Abdurrahman Sezginer, Monte Sereno, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/641,150

(22) Filed: Jul. 3, 2017

(65) Prior Publication Data

US 2017/0309008 A1      Oct. 26, 2017

Related U.S. Application Data

(63) Continuation of application No. PCT/US2016/045749, filed on Aug. 5, 2016, which is a continuation-in-part of application No. 14/822,571, filed on Aug. 10, 2015, now Pat. No. 9,547,892.

(51) Int. Cl.
*G06T 7/00* (2017.01)
*G01N 21/956* (2006.01)
(Continued)

(52) U.S. Cl.
CPC ........... *G06T 7/001* (2013.01); *G01N 21/956* (2013.01); *G03F 1/84* (2013.01); *G03F 7/705* (2013.01);
(Continued)

(58) Field of Classification Search
CPC ......... G06T 7/0006; G06T 7/00; G06T 7/001; G01N 21/956
See application file for complete search history.

(56) References Cited

U.S. PATENT DOCUMENTS 6,578,188 B1 *  6/2003  Pang .......................... G03F 1/26
                                                                    716/52
6,902,855 B2    6/2005  Peterson et al.
(Continued)

FOREIGN PATENT DOCUMENTS

CN       101969025 B      7/2013
JP       2004157518 A     6/2004
(Continued)

OTHER PUBLICATIONS

Sven van Haver et al, "General imaging of advanced 3D mask objects based on the fully-vectorial extended Nijboer-Zernike (ENZ) theory", 2008, Proc. SPIE 6924, Optical Microlithography XXI, 9 pages (Year: 2008).*

(Continued)

*Primary Examiner* — David F Dunphy
(74) *Attorney, Agent, or Firm* — Kwan & Olynick LLP

(57) ABSTRACT

Disclosed are methods and apparatus for qualifying a photolithographic reticle. A reticle inspection tool is used to acquire images at different imaging configurations from each of a plurality of pattern areas of a test reticle. A reticle near field for each of the pattern areas of the test reticle is recovered based on the acquired images from each pattern area of the test reticle. A lithography model is applied to the reticle near field for the test reticle to simulate a plurality of test wafer images, and the simulated test wafer images are analyzed to determine whether the test reticle will likely result in an unstable or defective wafer.

22 Claims, 7 Drawing Sheets

(51) Int. Cl.
*G03F 1/84* (2012.01)
*G03F 7/20* (2006.01)

(52) U.S. Cl.
CPC .............. *G01N 2021/95676* (2013.01); *G06T 2207/10144* (2013.01); *G06T 2207/10152* (2013.01); *G06T 2207/30148* (2013.01)

(56) References Cited

U.S. PATENT DOCUMENTS

| | | | |
|---|---|---|---|
| 7,418,124 | B2 | 8/2008 | Peterson |
| 7,646,906 | B2 | 1/2010 | Saidin et al. |
| 7,703,069 | B1 | 4/2010 | Liu et al. |
| 7,769,225 | B2 | 8/2010 | Kekare et al. |
| 7,820,341 | B2 | 10/2010 | Laidig et al. |
| 7,873,204 | B2 | 1/2011 | Wihl et al. |
| 7,932,004 | B1 | 4/2011 | Xiong et al. |
| 7,995,832 | B2 | 8/2011 | Xiong et al. |
| 8,102,408 | B2 | 1/2012 | Verma et al. |
| 8,423,927 | B2 | 4/2013 | Saied et al. |
| 8,594,823 | B2 | 11/2013 | Park et al. |
| 8,938,694 | B2 | 1/2015 | Liu et al. |
| 9,547,892 | B2 | 1/2017 | Shi et al. |
| 2002/0019729 | A1* | 2/2002 | Chang ................ G03F 1/26 703/6 |
| 2004/0109601 | A1* | 6/2004 | Pang ................ G03F 1/84 382/149 |
| 2004/0179726 | A1 | 9/2004 | Burdorf et al. |
| 2005/0244728 | A1* | 11/2005 | Liu ................ G03F 1/36 430/5 |
| 2006/0051682 | A1 | 3/2006 | Hess et al. |
| 2006/0206852 | A1* | 9/2006 | Khoh ................ G03F 1/36 716/53 |
| 2006/0236294 | A1 | 10/2006 | Saidin et al. |
| 2006/0242619 | A1* | 10/2006 | Pang ................ G03F 1/84 716/139 |
| 2008/0127027 | A1 | 5/2008 | Gallatin et al. |
| 2008/0204690 | A1 | 8/2008 | Berger et al. |
| 2009/0016595 | A1 | 1/2009 | Peterson et al. |
| 2010/0005440 | A1 | 1/2010 | Viswanathan et al. |
| 2010/0080443 | A1 | 4/2010 | Preil et al. |
| 2010/0162197 | A1 | 6/2010 | Ye et al. |
| 2010/0169060 | A1* | 7/2010 | Zhu ................ G03F 7/705 703/2 |
| 2010/0325761 | A1* | 12/2010 | Nakata ................ B82Y 15/00 850/33 |
| 2011/0276935 | A1 | 11/2011 | Fouquet et al. |
| 2011/0299759 | A1 | 12/2011 | Shi et al. |
| 2013/0058558 | A1 | 3/2013 | Ueno et al. |
| 2013/0232454 | A1 | 9/2013 | Chou et al. |
| 2013/0283217 | A1 | 10/2013 | Fujimura et al. |
| 2014/0254913 | A1 | 9/2014 | Pang |
| 2015/0054940 | A1 | 2/2015 | Shi et al. |
| 2015/0058814 | A1 | 2/2015 | Cai |
| 2015/0186069 | A1 | 7/2015 | Sharma et al. |
| 2016/0012579 | A1 | 1/2016 | Shi et al. |

FOREIGN PATENT DOCUMENTS

| | | |
|---|---|---|
| JP | 2005538425 A | 12/2005 |
| WO | 2018212787 A1 | 11/2018 |

OTHER PUBLICATIONS

Wong et al, "Level-Specific Lithography Optimization for 1-Gb DRAM", 2000, IEEE Transactions on Semiconductor Manufacturing, vol. 13, No. 1, 12 pages (pp. 76-87) (Year: 2000).*
"U.S. Appl. No. 14/822,571, Notice of Allowance dated Sep. 12, 2016", 10 pages.
"International Application Serial No. PCT/US2016/045749, Search Report dated Nov. 7, 2016", 3 pgs.
Howard, William B. et al., "Production Evaluation of Automated Reticle Defect Printability Prediction Application", Mask and Lithography Conference, 23rd European, Jan. 2007, 2 pgs.
CN Office Action, International Search Report, dated Jun. 16, 2017, Application No. 201580023431.2, filing date May 4, 2015, priority date May 6, 2014.
International Search Report for International Application No. PCT/US2017/064327, International Filing Date Dec. 1, 2017.
TW Office Action, International Search Report, dated Jun. 1, 2018, Application No. 104114492, filing date May 6, 2015, priority date May 6, 2015. English Translation 3 pages. Original TW document 3 pages.

* cited by examiner

APPARATUS AND METHODS FOR PREDICTING WAFER-LEVEL DEFECT PRINTABILITY

CROSS-REFERENCE TO RELATED APPLICATIONS

This application is a continuation of and claims the benefit under 35 U.S.C. § 120 to PCT Application No. PCT/US2016/045749, filed Aug. 5, 2016 by Abdurrahman Sezginer et al, which claims the benefit of priority of prior application U.S. application Ser. No. 14/822,571, filed 10 Aug. 2015, now U.S. Pat. No. 9,547,892, issued 17 Jan. 2017 by Abdurrahman Sezginer et al. These applications are herein incorporated by reference in their entirety for all purposes.

TECHNICAL HELD OF THE INVENTION

The invention generally relates to the field of reticle inspection. More particularly the present invention relates to pattern qualification.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

An integrated circuit is typically fabricated from a plurality of reticles. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device. The reticle writer uses the circuit pattern data to write (e.g., typically, an electron beam writer or laser scanner is used to expose a reticle pattern) a plurality of reticles that will later be used to fabricate the particular IC design.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication processes.

After fabrication of each reticle or group of reticles, each new reticle typically is qualified for use in wafer fabrication. For example, reticle patterns need to be free of printable defects. Thus, there is a continuing need for improved reticle inspection and qualification techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of qualifying a photolithographic reticle is disclosed. A reticle inspection tool is used to acquire images at different imaging configurations from each of a plurality of pattern areas of a test reticle. A reticle near field for each of the pattern areas of the test reticle is recovered based on the acquired images from each pattern area of the test reticle. A lithography model is applied to the reticle near field for the test reticle to simulate a plurality of test wafer images, and the simulated test wafer images are analyzed to determine whether the test reticle will likely result in an unstable or defective wafer.

In a further implementation, using a reticle inspection tool, images are acquired at different imaging configurations from each of a plurality of pattern areas of a calibration reticle. The reticle near field for each of the pattern areas of the calibration reticle is recovered based on the acquired images from each pattern area of the calibration reticle. Using the recovered reticle near field for the calibration reticle, wafer images are simulated based on the reticle near field. A parameter of the lithography model is adjusted so that simulated wafer images agree with wafers printed using the calibration reticle. In a specific implementation, the lithography model is based on a recovered reticle near field from a reticle. In a further aspect, the reticle near field is recovered using a quasi-Newton or conjugate gradient technique for determining the reticle near field. In another aspect, the reticle near field is recovered by a regressive technique that minimizes a sum of a plurality of squared differences between the acquired images and images that are calculated from the reticle near field. In another embodiment, the reticle near field is recovered using a Hopkins approximation. In another example, the reticle near field is recovered without using a design database that was used to fabricate the reticle. In one aspect, the acquired images include at least three images that are acquired at different imaging conditions that are selected to result in a same reticle near field. In a further aspect, the different process conditions include different focus settings, different illumination directions or patterns, different linear polarization for an entire illumination pupil or different parts of an illumination pupil, and/or different apodization settings to obscure different portions of a collection beam.

In another embodiment, the lithography model simulates a photolithography process, including the effect of a particular photoresist material. In one aspect, the lithography model is generated by comparing wafer images resulting from the model with reference images of a wafer that was fabricated using the calibration reticle and adjusting model parameters of the model until a difference between the acquired and reference images is minimized. In another aspect, the calibration reticle is also used to calibrate an optical proximity correction (OPC) model. In a specific implementation, the model is applied to the test reticle near field under different lithography process conditions. In this aspect, analyzing the simulated test wafer images includes determining whether the test reticle will likely result in an unstable wafer under the different lithography process conditions by comparing the simulated test images having different process conditions and that are associated with a same reticle area. In a further aspect, the test reticle is determined to be unstable when comparing the simulated test images results in a difference above a predefined threshold. In yet a further aspect, different reticle areas have different predefined thresholds.

In a further application, the method includes repairing the test reticle, discarding the test reticle, or monitoring particular areas of a wafer that is fabricated with such test reticle based on a determination that the test reticle will likely result in an unstable or defective wafer. In another aspect, the simulated test images are analyzed by comparing the simulated test images to images formed from the pre-OPC design database to determine whether the test reticle will likely result in an unstable or defective wafer.

In an alternative embodiment, the invention pertains to an inspection system for qualifying a photolithographic reticle. The system includes a light source for generating an incident beam and an illumination optics module for directing the incident beam onto a reticle. The system also includes a collection optics module for directing an output beam from each pattern area of the reticle to at least one sensor and at least one sensor for detecting the output beam and generating an image or signal based on the output beam. The system further comprises a controller that is configured to perform the following operations: (i) causing an acquiring of a plurality of images at different imaging configurations from each of a plurality of pattern areas of a test reticle, (ii) recovering a reticle near field for each of the pattern areas of the test reticle based on the acquired images from each pattern area of the test reticle, (iii) applying a lithography model to the reticle near field for the test reticle to simulate a plurality of test wafer images, (iv) analyzing the simulated test wafer images to determine whether the test reticle will likely result in an unstable or defective wafer. The controller and system may also be further configured to perform any of the above described method operations.

These and other aspects of the invention are described further below with reference to the figures.

DETAILED DESCRIPTION OF EXAMPLE EMBODIMENTS

Figure 1:
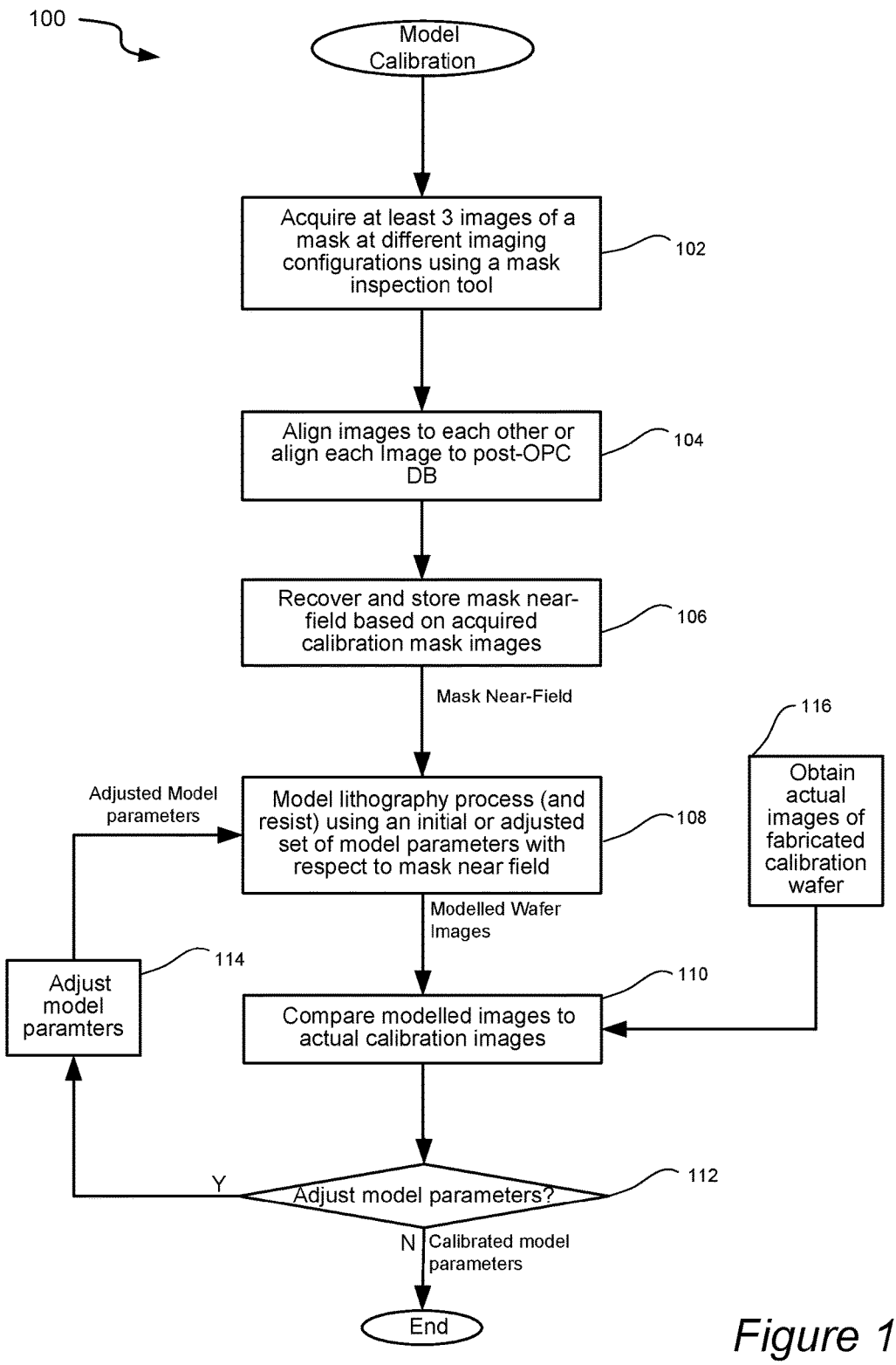
FIG. 1 is a flow chart illustrating a model calibration procedure in accordance with one embodiment of the present invention.

In the following description, numerous specific details are set forth in order to provide a thorough understanding of the present invention. The present invention may be practiced without some or all of these specific details. In other instances, well known process operations or apparatus components have not been described in detail to not unnecessarily obscure the present invention. While the invention will be described in conjunction with the specific embodiments, it will be understood that it is not intended to limit the invention to the embodiments.

The terms "reticle", "mask", and "photomask" are used herein interchangeably and generally each may include a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material.

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, a chromeless phase lithography PSM, and chromeless phase lithography (CPL). A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs), such as ArF and KrF masks. If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

It would be beneficial to detect each mask's defects prior to fabricating wafers using such mask or prior to shipping masks to a fabrication facility. One embodiment of the present invention includes techniques for qualifying a mask by predicting wafer-level behaviors using images of such reticle obtained from an inspection tool. A model for predicting wafer-level behavior is first generated from reticle images from a reticle, such as a calibration reticle, and such model can then be used in defect detection at a wafer-level based on reticle images of a same or other reticle.

Calibration Embodiments

Certain embodiments of the present invention provide techniques for calibrating a lithography model based on a mask near field that is recovered from a calibration mask, and this calibrated model can later be used during defect detection or other purposes as further described below with respect to model-use embodiments. Such a calibration process results in a more accurate lithography model, as compared to other techniques such as a calibration process that is based on the design database. A design database approach assumes that the geometric shapes in the design database accurately represent patterns on the fabricated mask, which is typically not the case. Other calibration techniques make assumptions that the fabricated mask's patterns and materials can be accurately represented by preselected three-dimensional profiles and a set of material property descriptions. In contrast, certain calibration embodiments as described herein avoid these modeling deficiencies by utilizing a mask near field that is recovered from the actual reticle so as to accurately calibrate a lithography model.

FIG. 1 is a flow chart illustrating a model calibration procedure 100 in accordance with one embodiment of the present invention. The following calibration process 100 for a particular reticle or set of reticles may be performed prior to fabrication of any wafers with such reticle(s) or prior to commencement of high volume wafer fabrication.

Initially, at least three images of a calibration mask are acquired at different imaging configurations using a mask inspection tool in operation 102. Alternatively, two images may be used, but using three images has been found to work well. In certain embodiments described herein, the results of this calibration process can eventually be used for defect detection for other reticles based on reticle images. Therefore, the images of the calibration reticle are preferably acquired with the detector of the reticle inspection system that will be used for inspection of the other reticles or a similarly configured detector of a similarly configured reticle inspection system (e.g., a different reticle inspection system of the same make and model as the reticle inspection system that will be used for inspection). In other words, the images that may be used for calibration are preferably acquired under the same optical conditions as will be used for inspection. In this manner, the interaction of the reticle with the illuminating electromagnetic waves may be measured as directly as possible.

The calibration reticle should have characteristic(s) that are substantially similar to the reticle to be inspected for defect detection or to be measured for metrology purposes. For example, the calibration reticle and the test reticle are preferably formed from substantially the same materials having substantially the same thicknesses and compositions. In addition, the two reticles may have been formed using the same processes. The two reticles may not necessarily have the same patterns printed thereon as long as the patterns on the reticles can be broken up into segments that are substantially the same (e.g., lines having similar widths, etc.). In addition, the reticle that will be inspected and the reticle that is used to acquire the images may be one and the same reticle.

The three or more images may then be aligned with each other or each image may be aligned to the post-OPC database in operation 104. For instance, the acquired images may be aligned via spatial-domain or frequency-domain methods. Alignment adjustments may depend on specific geometries of an inspection system that is used. If different images are obtained using different collection paths, some adjustment of the images can be made to compensate for differences in optical paths.

In lithography and inspection, a reticle having various patterns is illuminated by electromagnetic (EM)-waves that are incident from many directions. This incident light is diffracted from different points of the mask pattern at different electromagnetic field phases which interfere with each other differently. The near-field of the reticle is the electromagnetic field at a proximate distance of a few wavelengths from the reticle.

The collection optics generally directs a diffraction-limited portion of the light from the reticle towards a detector (or wafer) to form an image. The detector detects intensity which is the result of interference due to the mask near field, but does not detect the phase.

Although far-filed intensity is obtained in the detected signals, it is desirable to recover the mask near field, which includes amplitude and phase. In the illustrated embodiment, the mask near field is recovered and stored based on such acquired calibration mask images, as illustrated in operation 106. Multiple images (or signals) are generally used to recover the mask near field, which includes both phase and amplitude components. The near-field data may be determined by a regression technique based on the images acquired from the reticle. For example, the near-field of a selected portion of the reticle can be recovered (regressed), using a quasi-Newton or conjugate gradient technique, from its acquired optical images or intensity of images recorded at a detector plane. In addition, any other suitable regression method and/or algorithm may be used to determine the near-field data from the one or more actual images.

In particular, recovering the near-field of a reticle from its intensity images is an inverse problem or a regression problem. The near-field can be recovered iteratively by minimizing a cost function (e.g., energy or penalty function). The quantity that is minimized can be the sum of squared differences between the acquired images and intensity images at the detector that are calculated from the mask near-field. In other words, intensity images can be calculated from the final mask near field for various sets of optical system properties, and these calculated images will most closely match the acquired images when the mask near field is found. Refer to U.S. application Ser. No. 14/702,336 for more details on the mask near field recovery methodology.

In the case where multiple images are acquired under various optical conditions, the recovered near field mask m, which carries the phase and amplitude information, can be determined by the following equation:

$$m = \mathrm{argmin} \sum_{\alpha} c_{\alpha} \sum_{x,y} \left[ I_{\alpha} - \sum_{i} \lambda_i^{(\alpha)} |m \otimes \psi_i^{(\alpha)}|^2 \right]^2$$

In the above equation, $I_{\alpha}$ is the measured image for imaging condition $\alpha$, $\psi_i^{(\alpha)}$ is a set of eigenvectors describing the inspection imaging system, $\lambda_i^{(\alpha)}$ is a set of corresponding eigenvalues for the imaging system, and $c_{\alpha}$ is a non-negative weighting factor between 0 and 1. The above equation can be solved iteratively through, for example, methods such as quasi-Newton or conjugate gradient.

Various suitable combinations of illumination and/or collection configurations may be utilized. The different imaging configurations are generally selected to provide images from which the mask near field may be calculated. Any suitable imaging or optical configurations may be selected so that the mask near field remains the same under the different operating conditions. Examples include different focus settings, different illumination directions or patterns, different linear polarization for the entire illumination pupil or different parts of the illumination pupil, different apodization settings to obscure different portions of the collection beam, etc. For instance, different quadrants of the illumination pupil may have different polarization settings. In another example, the imaging configurations may include high resolution images, such as transmitted images (e.g., for ArF masks) with different pupil shapes and/or different focal conditions. In another embodiment, three or more reflected images with different pupil shapes and/or different focal conditions may be obtained (e.g., for EUV masks).

The reticle may be imaged using a relatively low NA (e.g., less than 0.5). In contrast, a "substantially high resolution image" generally refers to an image of a reticle in which features printed on the reticle appear substantially as they are formed on the reticle (within the optical limitations of the reticle inspection system used to generate the image). For example, a "substantially high resolution image" of a reticle is an image that is generated by imaging the physical reticle at the reticle plane with a substantially high resolution reticle inspection system (e.g., a numerical aperture (NA) of greater than 0.8). In contrast, a "substantially low NA" used to generate an image of a reticle may be an NA that is less than 0.5. In addition, the "substantially low NA" used to generate a reticle image may be substantially the same as the NA on the reticle side that is used by an exposure system to project an image of the reticle onto a wafer thereby transferring features on the reticle onto the wafer. Therefore, in the substantially low NA image (or LNI), the reticle features may have a substantially different appearance than the actual reticle features. For example, reticle features may appear to have more rounded corners in an LNI of a feature than the actual feature that is formed on the reticle.

Acquisition with different imaging configurations may be simultaneous or sequential. The acquired images do not have to be at the field planes. The two or more images can be acquired at the pupil planes. One example is the Gerchberg-Saxton algorithms in which a combination of field plane images and pupil plane diffraction orders can be utilized to solve both the amplitude and phase of the object.

In one embodiment, the mask near field may be determined based on the acquired images via a Hopkins approximation. In another embodiment, the regression does not include thin-mask approximations. For example, the near-field of the reticle is the electromagnetic field that is calculated to be present near the surface of the reticle when it is illuminated by a normally-incident plane wave. In lithography and inspection, a reticle is illuminated by plane-waves that are incident from many directions. When the direction of incidence changes, according to the Hopkins approximation, the directions of the diffraction orders change but their amplitudes and phases remain approximately unchanged. The embodiments described herein can use the Hopkins' phase approximation but do not make the so-called thin-mask or Kirchhoff approximations.

The actual mask may vary from the intended design patterns due to the mask writing process. Obtaining the near field mask from images of the mask means that such near field mask is obtained from the actual physical mask, rather than the design database. That is, mask near field may be recovered without using the design database.

Once the near field mask is recovered, it can be used for any number of applications. For defect detection, the printability of a reticle defect on the wafer is important, and the printability of reticle defects depends directly on the reticle near field and lithography system. As an interesting note, the interference of the mask electromagnetic field vectors as a result of a higher NA will be greater (than a lower NA inspection system) due to the wider range of incident angles of light and associated interfering electric field components for a higher NA.

In one embodiment, a reticle qualification is performed by assessing whether the recovered mask near field will likely result in wafer pattern defects under simulated wafer fabrication conditions. In the illustrated procedure, the photolithography process and photoresist can be modeled using an initial set of model parameters with respect to the near field mask in operation 108. The model may include just the effect of the photolithography scanner, and/or it may also include the effect of resist, etch, CMP or any other wafer processes. One example process simulation tool is Prolith available from KLA-Tencor Corp. of Milpitas, Calif.

The input for the model and its modeling parameters includes a set of process conditions. That is, the model is configured to simulate different sets of process conditions on the reconstructed near field mask. Each set of process conditions generally corresponds to a set of wafer manufacturing process parameters that characterize, or partially characterize the wafer process for forming a wafer pattern from the mask. For example, a particular setting of focus and exposure can be input to the model. Use of such model with different sets of process conditions can result in a set of simulated wafer or resist pattern images formed by the reconstructed near field mask under different processing conditions, and these simulated wafer images can be used for defect detection as further described herein.

The calibration reticle is also used to fabricate a calibration wafer from which actual images are obtained in operation 116. In one example, the actual images are acquired using a critical dimension (CD) scanning electron microscope (SEM). Other imaging tools may be utilized, but a high resolution tool is preferred.

In general, the calibration wafer will contain any number of structures, which may widely vary. The structures may be in the form of gratings which are typically periodic. Each grating may be periodic in one direction (X or Y) as, for example, a line space grating, or it may be periodic in two directions (X and Y) as, for example, a grid space grating. Examples of a grid space grating may include an array of lines in the Y direction with each line being segmented in the X direction. Another grid space example is an array of dot structures. That is, each structure may take the form of a line space grating, grid space grating, checkerboard pattern structure, etc. The structure design characteristics may each include line width (width at a specific height), line space width, line length, shape, side wall angle, height, pitch, grating orientation, top-profile (degree of top rounding or T topping), bottom profile (footing), etc. The calibration water may contain structures with different combinations of these feature characteristics. As should be appreciated, different structure characteristics (such as different widths, spacing, shapes, pitch, etc.) exhibit different response to focus and, therefore, the calibration mask preferably includes different structures with different characteristics.

In an alternative embodiment, the calibration wafer may take the form of a "Design of Experiments (DOE) wafer having different measurement sites that were subject to different processing conditions. In more general embodiments, process parameter variations are organized in a pattern on the surface of a semiconductor wafer (referred to as a DOE wafer). In this manner, the measurement sites correspond to different locations on the water surface having different associated process parameter values. In one example, the DOE pattern is a Focus/Exposure Matrix (FEM) pattern. Typically, a DOE water exhibiting a FEM pattern includes a grid pattern of measurement sites. In one grid direction (e.g., the x-direction), the exposure dosage is varied while the depth of focus is held constant. In the orthogonal grid direction (e.g., the y-direction), the depth of focus is varied while the exposure dosage is held constant. In this manner, measurement data collected from the FEM wafer includes data associated with known variations in the focus and dosage process parameters.

FEM measurement sites are generally located across the focus exposure matrix wafer. In fact, there may generally be one or more measurement sites per field. Each field may be formed using a different combination of focus and exposure (or may be focus or exposure only). For example, a first field may be produced using a first combination, and a second field may be produced using a second combination that is different than the first combination. The multiple combinations can be produced using varying focus and varying exposure, varying focus—constant exposure, constant focus—varying exposure, and the like.

The number of measurement sites may also differ. The number of sites per field is generally smaller on production wafers since the real estate on production wafers is so valuable. Also, fewer measurements are made on a product wafer than on a focus exposure matrix wafer due to time constraints in production. In one embodiment, a single site is measured per field. In another embodiment, multiple sites are measured per field.

In most FEM cases, the measurement site structures are formed from identically designed patterns using different processing parameters. It should be noted, however, that different focus exposure matrices may have different structures. For example, a first matrix may be performed using a first grating type and a second matrix may be performed using a second grating type that is different than the first grating type.

In general, optical signal data associated with known variation of any set of process parameters, structural parameters, or both, are contemplated. Regardless of form, the calibration wafer structures may be printed in a variety of different wafer layers. In particular, the printed structures are generally printed in a layer of photoresist using standard lithography processes (e.g., projecting a circuit image through a reticle and onto a silicon wafer coated with photoresist). The wafer may be a calibration wafer with layers of materials that correspond to the materials typically present on product wafers at that step in the test process. The printed structures may be printed over other structures in underlying layers. The calibration wafer may be a product wafer that has the potential to produce working devices. The calibration wafer may be a simple wafer that is only used for calibrating the model. The calibration wafer may be the same wafer that is used to calibrate the OPC design model. More than one calibration wafer may be used to calibrate the lithography model. When using multiple calibration wafers, the same or different calibration reticles may be used. The different calibration reticles may have patterns with different dimensions so as to produce a wider range of image data.

The process parameters used to form the calibration structures are generally configured to keep the calibration structures' characteristics within desired specifications. The calibration structures may be printed on a calibration wafer as a part of a calibration procedure or they may be printed on a production wafer during production. In production, the calibration structures are typically printed in the scribe line between device areas (e.g., dies that define the IC) disposed on a production wafer. The measurement sites may be dedicated calibration structures disposed around the device structures or they may be a portion of the device structure (e.g., a periodic portion). As should be appreciated, using a portion of the device structure may be more difficult, but it tends to be more accurate since it is a portion of the device structure. In another embodiment, the calibration structures may be printed across an entire calibration wafer.

Referring back to FIG. 1, corresponding modeled images and calibration images may be compared in operation 110. It may then be determined whether the model parameters are to be adjusted in operation 112. If model parameters are to be adjusted, they are adjusted in operation 114 and the procedure 100 repeats the operation 108 for modeling the lithography process (and resist) using the adjusted parameters. Model parameters may be adjusted until the differences between the model and calibration images have reached a minimum that is also below a predefined threshold. The quantity that is minimized can be the sum of squared differences between the acquired calibration images and the simulated images. The output of this process 100 is a lithography/resist model and its final model parameters. This set of model parameters, by the nature of using mask near field, overcomes the technical hurdle associated with mask process modeling and mask 3D topography modeling.

Model Use Embodiments:

After a final calibrated lithography/resist model for a particular process is obtained, such model may be used to generate accurate wafer plane resist images (e.g., after development or after etch) from a mask prior to wafer fabrication with such mask. These resist images will allow one to assess the wafer images for any inspection patterns with high fidelity and through different focus and exposure settings. Since this assessment process can occur prior to wafer fabrication, qualification and defect detection cycles can be significantly shortened.

Figure 2A:
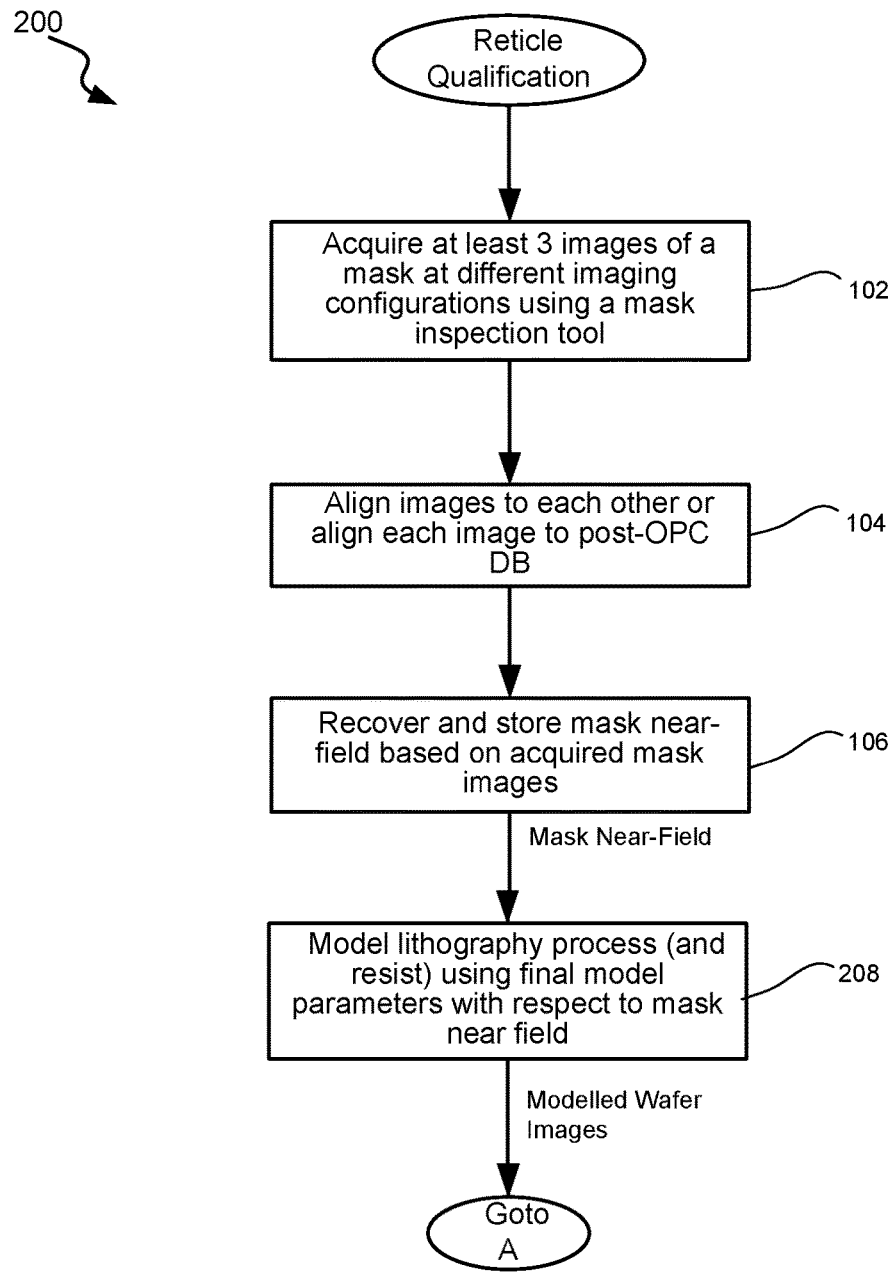
FIGS. 2A and 2B illustrate a flow chart representing a reticle qualification process in accordance with one embodiment of the present invention.
Figure 2B:
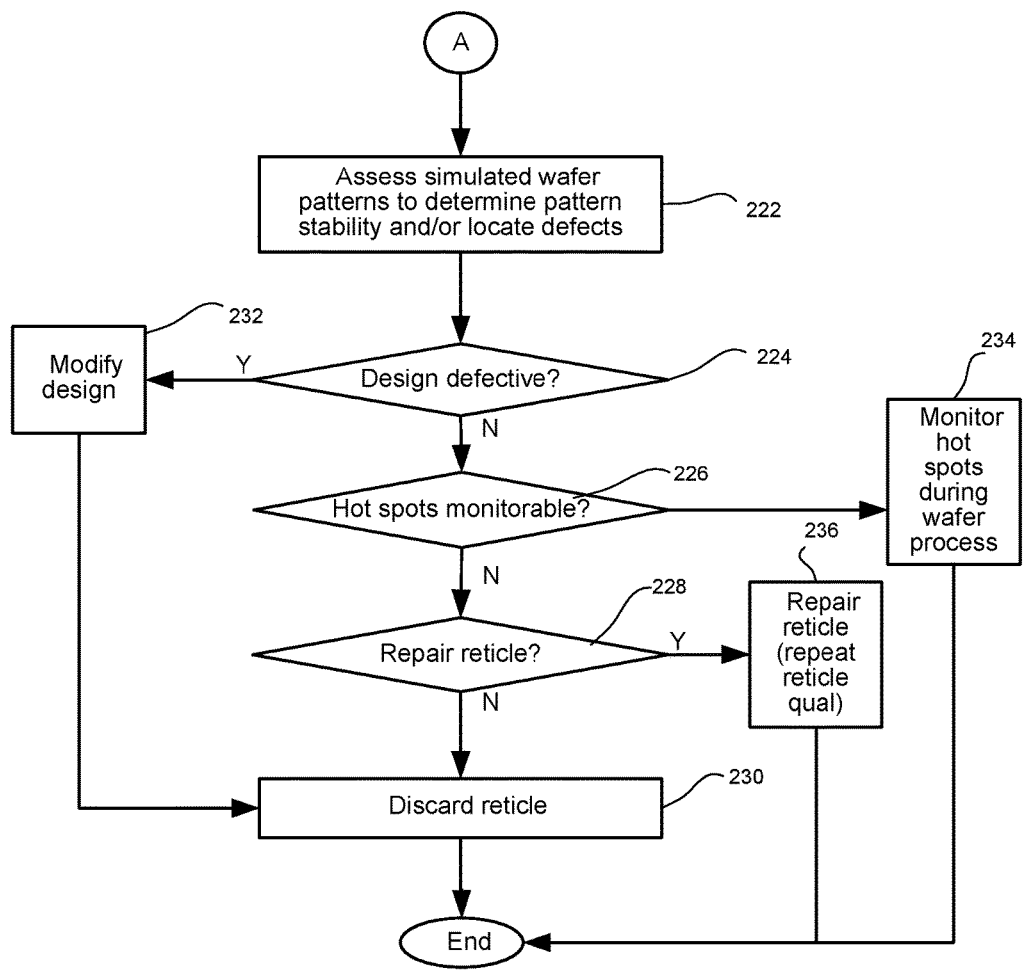

FIGS. 2A and 2B illustrate a flow chart representing a reticle qualification process 200 in accordance with one embodiment of the present invention. In general, a mask near field is obtained for a particular reticle in operations 102, 104, and 106 based on images acquired from such particular reticle. These operations are similar to the same referenced operations of FIG. 1. After a mask near field is obtained, the lithography process (and resist) may be modeled using the final model parameters with respect to the calculated near mask field in operation 208. For instance, the model that was calibrated with a calibration wafer is used to model wafer images using a mask near field.

Figure 3A:
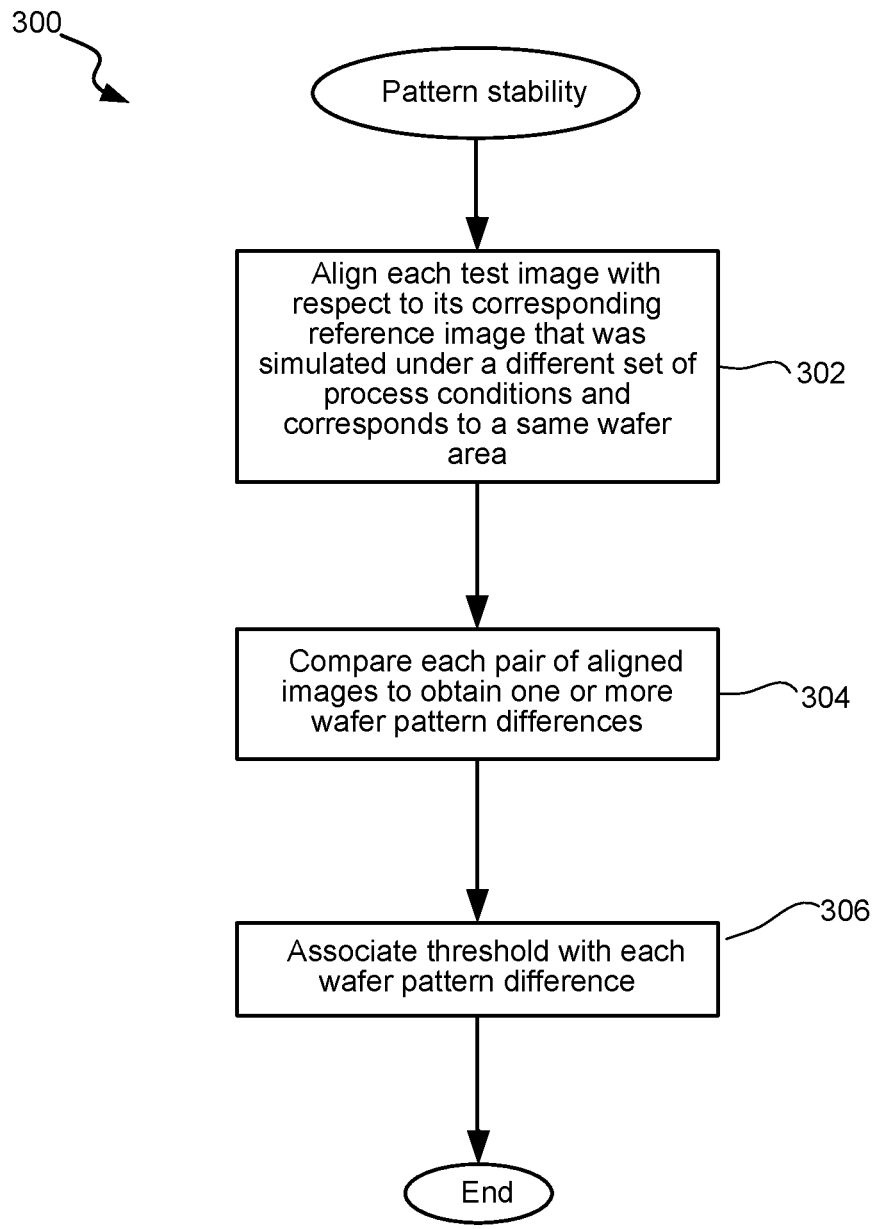
FIG. 3A is a flow chart illustrating a process for determining reticle pattern stability in accordance with an example application of the present invention.

Referring to FIG. 2B, it may then be determined whether a reticle will likely result in unstable or defective wafer patterns in operation 222. In one embodiment, the model may simply be applied to the mask near field using a plurality of different process conditions, such as focus and dose, to assess the reticle design stability under varying process conditions. FIG. 3A is a flow chart illustrating a process 300 for determining reticle pattern stability in accordance with an example application of the present invention. Initially, each test image, which is produced by the model, may be aligned with its corresponding reference image that was simulated under a different set of process conditions and corresponds to a same wafer area so as to obtain one or more wafer pattern differences in operation 302.

Each pair of aligned images may be compared to each other to obtain one or more wafer pattern differences in operation 304. Thresholds may then be associated with each wafer pattern difference in operation 306. The thresholds may be assigned to different areas of the reticle and, thereby, corresponding wafer patterns. The thresholds may all be the same or be different based on various factors, such as structure type, assigned MEEF (or Mask Error Enhancement Factor as described further below) level or hot spot identification, etc. For instance, different structures types may be given different thresholds. An initial set of hot spots may be optionally identified in both the reference and test mask pattern. For instance, a designer may provide a list of hot spot coordinates.

For example, areas defined as hot spots may be assigned one detection threshold, while non-hot spot areas may be assigned a higher threshold (for defect detection). This differentiation can be used to optimize inspection resources.

As densities and complexities of integrated circuits (ICs) continue to increase, inspecting photolithographic mask patterns become progressively more challenging. Every new generation of ICs has denser and more complex patterns that currently reach and exceed optical limitations of lithographic systems. To overcome these optical limitations, various Resolution Enhancement Techniques (RET), such as Optical Proximity Correction (OPC), have been introduced. For example, OPC helps to overcome some diffraction limitations by modifying photomask patterns such that the resulting printed patterns correspond to the original desired patterns. Such modifications can include perturbations to sizes and edges of main IC features, i.e., printable features. Other modifications involve additions of serifs to pattern corners and/or providing nearby sub-resolution assist features (SRAFs), which are not expected to result in printed features and therefore, are referred to as non-printable features. These non-printable features are expected to cancel pattern perturbations that would otherwise have occurred during the printing process. However, OPC makes mask patterns even more complex and usually very dissimilar to resulting wafer images. Furthermore, OPC defects often do not translate into printable defects. The increased complexity of the photomask pattern and fact that not all pattern elements are expected to directly affect the printed pattern makes the task of inspecting the photomask for meaningful pattern defects much more difficult. As the semiconductor industry moves to ever smaller features, leading-edge manufacturers are starting to use even more exotic OPC, such as inverse lithography technology all which result in highly complex patterns on the mask. Thus, it is highly desirable to know the mask writing fidelity and its wafer printing quality prior to physically making the wafer.

One measure of a defect's importance is its MEEF or Mask Error Enhancement Factor. This factor relates the size of the defect in the mask plane to the magnitude of the impact it will have on the printed image. High MEEF defects have high impact on the printed pattern; low MEEF defects have little or no impact on the printed pattern. An undersized main pattern feature in a dense fine-line portion of a pattern is an example of a defect with high MEEF where a small mask plane sizing error could cause a complete collapse of the printed pattern. An isolated small pinhole is an example of a defect with low MEEF where the defect itself is too small to print and is distant enough from the nearest main pattern edge so as not to affect how that edge is printed. As these examples show the MEEF of a defect is a somewhat complicated function of the defect type and the pattern context in which the defect is located.

In addition to higher MEEF mask defects causing more significant wafer defects, certain design patterns and corresponding mask patterns may be more robust than other design and mask patterns to process changes. When the fabrication process begins to drift from optimal process conditions, certain mask patterns may result in more significant wafer pattern perturbations and defects.

Referring back to FIG. 2B, it may then he determined whether the design is defective in operation 224. In one embodiment, it is determined whether the design pattern results in unacceptable wafer pattern variation under a specified range of process conditions (or process window). It is determined whether there is a significant difference due to process variability. If the difference between differently processed wafer patterns is higher than a corresponding threshold, such wafer patterns may be deemed defective. If the design is determined to be defective, the design may be modified in operation 232.

If the design is not deemed defective, it may then be determined whether the hot spots can be monitored in operation 226. If the hot spots are to be monitored, the hot spots can then be monitored during the wafer process in operation 234, for instance, as described further below. For instance, the hot spot patterns may be monitored during wafer fabrication to determine whether the process has drifted out of specification and has caused the corresponding wafer pattern to have critical parameters that change to unacceptable values. One implementation may involve setting a relatively high MEEF level for inspection of the corresponding hot spot's reticle and/or wafer pattern. As conditions get further away from nominal process conditions, CD or EPE can become large and endanger the integrity of the wafer manufacturing process.

Hot spot patterns may be identified merely when a test mask pattern changes by a predefined amount regardless of how such change compares to the original intended design (e.g., pre-OPC data). In other words, a significant change in the physical mask pattern under different process conditions may indicate a problem with the intended design pattern. Differences between the corresponding modeled image portions represent differences in the effect of the process conditions on the designed pattern and the manufactured mask Differences associated with a particular design pattern are commonly referred to as "design hot spots", or just "hot spots", and represent weak points in the design with respect to the particular process conditions that have been examined, maybe also, with respect to the manufactured mask. Examples of the kinds of differences that might be found between modeled images for different process conditions are CD (critical dimension) or EPE (edge placement error).

In another embodiment, if the model is applied to the post-OPC design database, the resulting wafer pattern can correspond to the pattern that is intended by the designer to be printed on the wafer. Optionally, the results from applying the model to the post-OPC database can be used with the modeled images to improve hot spot detection. For example, a model of the post-OPC database takes into account design effects only, and so can be used to separate the effect of the wafer process on the design and the effect of the wafer process on the manufactured mask. Modelled patterns from the mask near field may be compared to modelled wafer images from corresponding post-OPC patterns. For instance, when a set of modelled wafer patterns for different process changes match corresponding modelled post-OPC wafer patterns for the same process changes, the changes in wafer pattern (or resist pattern) due to process change can be determined to originate from the design pattern, which can be redesigned or monitored, rather than from a defect in the mask pattern. However, if the changes on wafer due to process variations from the post-OPC database are different from those on wafer due to the same process variations from the recovered mask (or mask near field), then these hot spots are considered originating from a hot spot from the actual mask, which can be repaired or monitored.

It may also be determined whether the reticle is to be repaired in operation 228. The anticipated water pattern variations may be determined to be out of specification for the process window that is expected to be used during the lithography process. In certain cases, the reticle may contain a defect that is repaired in operation 236. The reticle may then be requalified. Otherwise, the reticle may be discarded if it is not repairable in operation 230. A new reticle may then be manufactured and requalified.

Figure 3B:
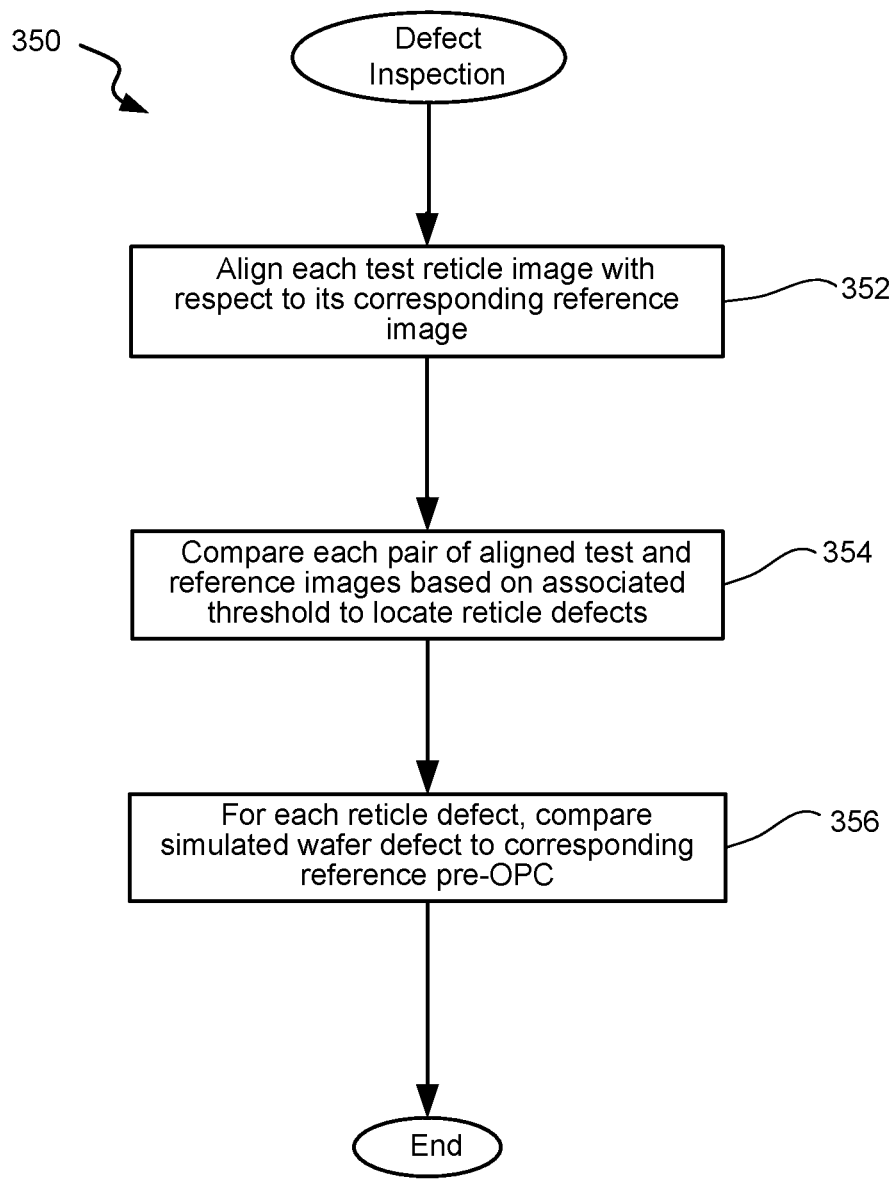
FIG. 3B is a flow chart illustrating a defect inspection procedure in accordance with an alternative embodiment of the present invention.

FIG. 3B is a flow chart illustrating a detect inspection procedure 350 in accordance with an alternative embodiment of the present invention. Initially, the reticle is inspected for defects. In operation 352, each test reticle image may be aligned with its corresponding reference image. In one embodiment, a die-to-die or cell-to-cell alignment may be accomplished. In another embodiment, the reticle image is aligned with a rendering of the corresponding post-OPC design. For instance, the post-UPC design is processed so as to simulate the reticle fabrication process and imaging of such design. For example, corners are rounded.

Each pair of aligned test and reference images is compared based on an associated threshold to locate reticle defects in operation 354. Any suitable mechanism may be used to associate thresholds to particular reticle areas as further described above.

For each reticle defect, the corresponding simulated wafer defect area may then be compared to its corresponding reference pre-UPC area in operation 356. That is, the simulated wafer patters are assessed to determine whether the reticle defect results in a wafer defect that varies from the intended design. The pre-UPC design patterns may also be further processed to model the inspection tool operation for imaging such design patterns.

Referring back to FIG. 2B, it may then be determined whether the reticle design is defective in operation 224. For instance, it may be determined whether any difference between a simulated wafer pattern for a reticle defect and its corresponding pre-OPC pattern is above a predefined threshold. The procedure 200 may continue so as to determine whether to monitor wafer hot spots, repair the reticle, or redesign the reticle as described above.

Certain techniques of the present invention provide mask pattern qualification and early detection of weak patterns or hot spots on the physical mask before beginning wafer manufacturing. Certain embodiments of the present invention provide more than mask near field recovery. In addition to providing recovery of the wafer pattern based on reticle images, a full range of wafer process effects including many settings of focus and exposure, and the effect of wafer resist, etch, CMP, and any other wafer processes, can be considered. No prior knowledge of the mask is required since the mask near field is recovered using only reticle images without using reticle design data. Since mask patterns are generally 4x larger than wafer patterns, more exact locations of patterns with respect to the design database can be determined. The above techniques can also be extended to any suitable type of masks, such as pattern qualification to EUV masks.

Figure 4:
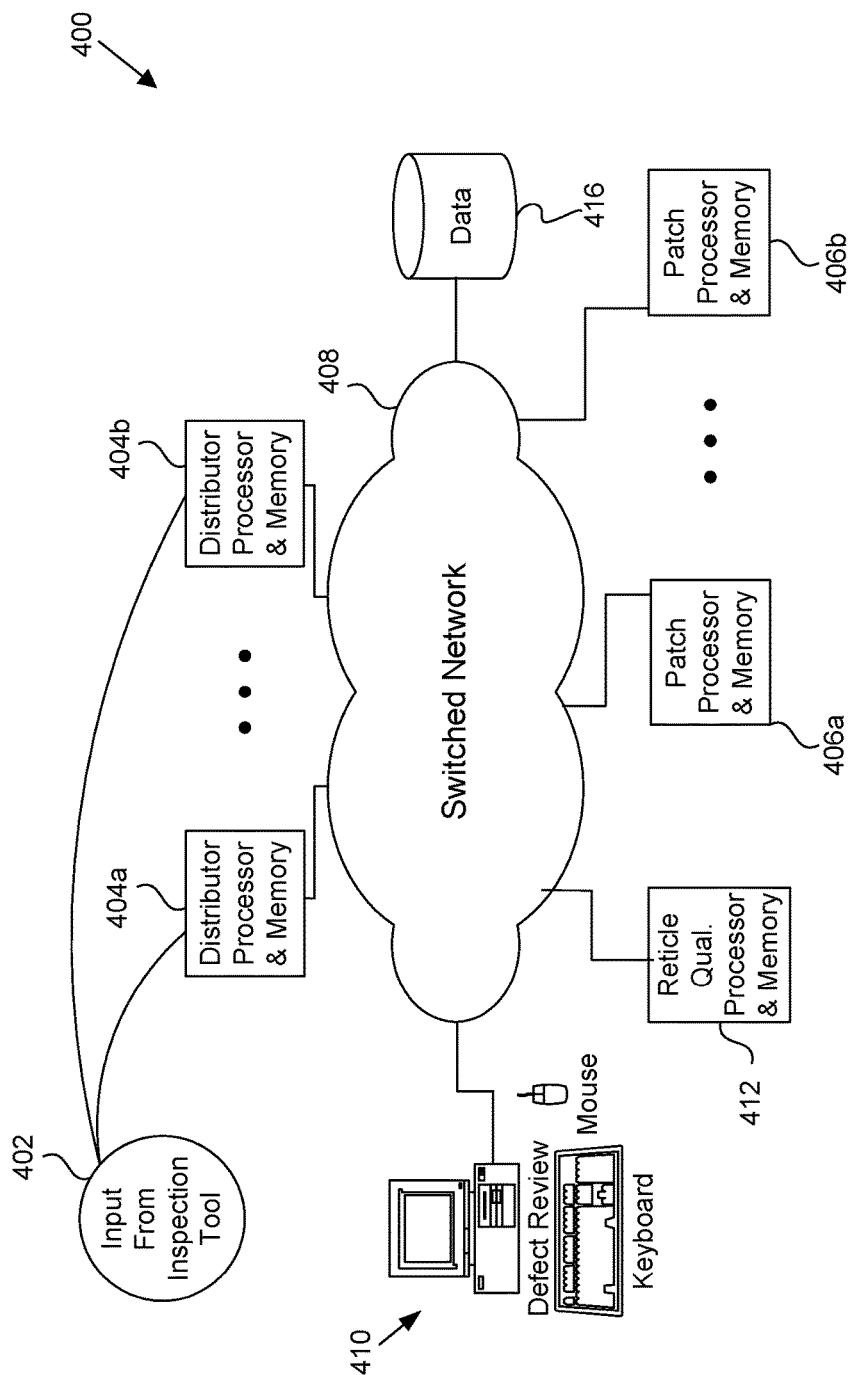
FIG. 4 is a diagrammatic representation of an example inspection system in which techniques of the present invention may be implemented.

Techniques of the present invention may be implemented in any suitable combination of hardware and/or software. FIG. 4 is a diagrammatic representation of an example inspection system 400 in which techniques of the present invention may be implemented. The inspection system 400 may receive input 402 from a high NA inspection tool or a low NA inspector mimicking a scanner (not shown). The inspection system may also include a data distribution system (e.g., 404a and 404b) for distributing the received input 402, an intensity signal (or patch) processing system (e.g., patch processors and reticle qualification system (e.g., 412) for mask near field and wafer recovery, process modelling, etc., a network (e.g., switched network 408) for allowing communication between the inspection system components, an optional mass storage device 416, and one or more inspection control and/or review stations (e.g., 410) for reviewing the identified hot spots, inspection results, etc. Each processor of the inspection system 400 typically may include one or more microprocessor integrated circuits and may also contain interface and/or memory integrated circuits and may additionally be coupled to one or more shared and/or global memory devices.

The inspector or data acquisition system (not shown) for generating input data 402 may take the form of any suitable instrument (e.g., as described further herein) for obtaining intensity signals or images of a reticle. For example, the low NA inspector may construct an optical image or generate intensity values of a portion of the reticle based on a portion of detected light that is reflected, transmitted, or otherwise directed to one or more light sensors. The low NA inspector may then output the intensity values or image.

The low NA inspection tool may be operable to detect and collect reflected and/or transmitted light as an incident optical beam scans across each patch of a reticle. As noted above, the incident optical beam may scan across reticle swaths that each comprises a plurality of patches. Light is collected in response to this incident beam from a plurality of points or subareas of each patch.

The low NA inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. Two or more images of the reticle may be generated after all the positions of the reticle are scanned and converted into detected signals, or portions of a two or more images may be generated as each reticle portion is scanned with the final two or more images for the reticle being complete after the entire reticle is scanned.

The detected signals may also take the form of aerial images. That is, an aerial imaging technique may be used to simulate the optical effects of the photolithography system so as to produce an aerial image of the photoresist pattern that is exposed on the water. In general, the optics of the photolithography tool are emulated so as to produce an aerial image based on the detected signals from the reticle. The aerial image corresponds to the pattern produced from the light passed through the photolithography optics and reticle onto the photoresist layer of a wafer. Additionally, the photoresist exposure process for the particular type of photoresist material may also be emulated.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrupole, quasar, annulus, etc. In a specific example, Source Mask Optimization (SMO) or any pixelated illumination technique may be implemented. The incident light may also be passed through a linear polarizer for linearly polarizing all or a portion of the illumination pupil in one or more polarizations. The detected light may be passed through apodization components for blocking particular areas of the collection beam.

Intensity or image data 402 can be received by data distribution system via network 408. The data distribution system may be associated with one or more memory devices, such as RAM buffers, for holding at least a portion of the received data 402. Preferably, the total memory is large enough to hold an entire swatch of data. For example, one gigabyte of memory works well for a swatch that is 1 million by 1000 pixels or points.

The data distribution system (e.g., 404a and 404b) may also control distribution of portions of the received input data 402 to the processors (e.g. 406a and 406b). For example, data distribution system may route data for a first patch to a first patch processor 406a, and may route data for a second patch to patch processor 406b. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well fur intensity values or an image corresponding to a patch that is 512 by 1024 pixels. Alternatively, the patch processors may share memory.

Each set of input data 402 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 406a, and the second memory partition may hold and route second data to patch processor 406b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 5A:
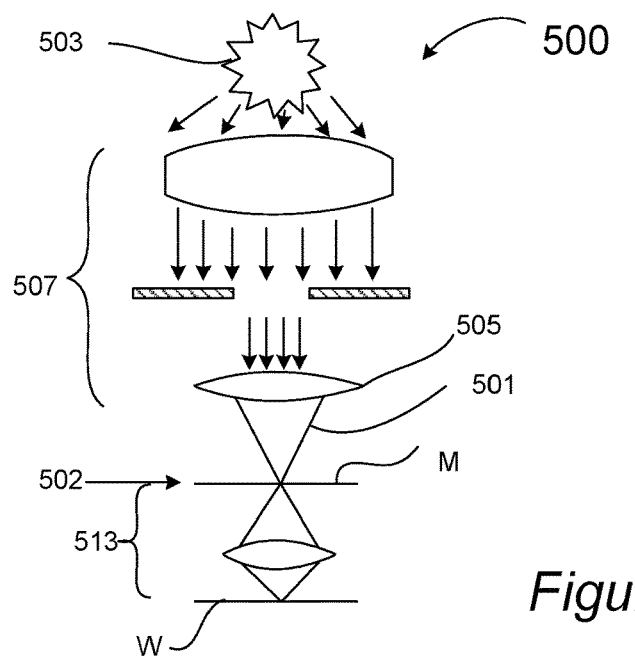
FIG. 5A is a simplified schematic representation of a lithographic system for transferring a mask pattern from a photomask onto a water in accordance with certain embodiments.

FIG. 5A is a simplified schematic representation of a typical lithographic system 500 that can be used to transfer a mask pattern from a photomask M onto a wafer W in accordance with certain embodiments. Examples of such systems include scanners and steppers, more specifically the TWINSCAN NXT:1970Ci Step-and-Scan system available from ASML in Veldhoven, Netherlands. In general, an illumination source 503 directs a light beam through an illumination optics 507 (e.g., lens 505) onto a photomask M located in a mask plane 502. Illumination lens 505 has a numeric aperture 501 at that plane 502. The value of the numerical aperture 501 impacts which defects on the photomask are lithographic significant defects and which ones are not. A portion of the beam that passes through the photomask M forms a patterned optical signal that is directed through imaging optics 513 and onto a wafer W to initiate the pattern transfer.

Figure 5B:
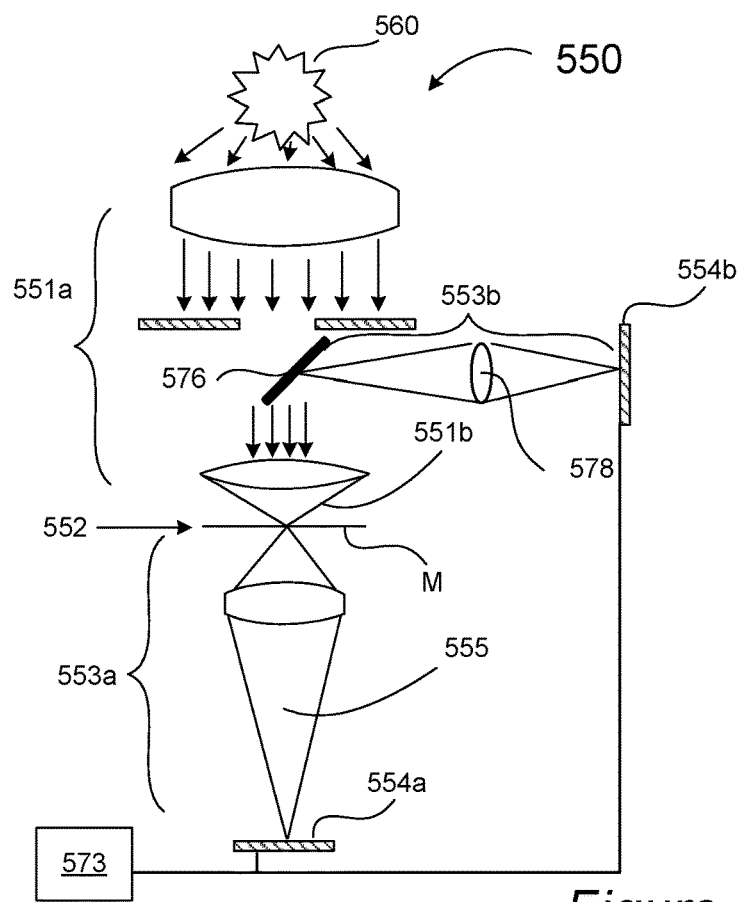
FIG. 5B provides a schematic representation of a photomask inspection apparatus in accordance with certain embodiments.

FIG. 5B provides a schematic representation of an example inspection system 550 that has illumination optics 551a includes an imaging lens with a relative large numerical aperture 551b at a reticle plane 552 in accordance with certain embodiments. The depicted inspection system 550 includes detection optics 553a and 553b, including microscopic magnification optics designed to provide, for example, 60-200× magnification or more for enhanced inspection. For example, numerical aperture 551b at the reticle plane 552 of the inspection system may be considerable greater than the numerical aperture 501 at the reticle plane 502 of the lithography system 500, which would result in differences between test inspection images and actual printed images.

The inspection techniques described herein may be implemented on various specially configured inspection systems, such as the one schematically illustrated in FIG. 5B. The illustrated system 550 includes an illumination source 560 producing a light beam that is directed through illumination optics 551a onto a photomask :M in the reticle plane 552. Examples of light sources include a coherent laser light source (e.g., deep UV or gas laser generator), a filtered lamp, LED light source, etc. In one example, the source is a 193 nm laser. As explained above, the inspection system 550 may have a numerical aperture 551b at the reticle plane 552 that may be equal to or greater than a reticle plane numerical aperture (e.g., element 501 in FIG. 5A) of the corresponding lithography system. The photomask M to be inspected is placed on a mask stage at the reticle plane 552 and exposed to the source.

The patterned image from the mask M is directed through a collection of optical elements 553a, which project the patterned image onto a sensor 554a. In a reflecting system, optical elements (e.g., beam splitter 576 and detection lens 578) direct and capture the reflected light from the mask M onto sensor 554b. Although two sensors are shown, a single sensor can be used to detect reflected and transmitted light during different scans of the same reticle area. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 554a and/or 554b) can be processed by a computer system 573 or, more generally, by one or more signal processing devices, which may each include an analog-to-digital converter configured to convert analog signals from each sensor into digital signals for processing. The computer system 573 typically has one or more processors coupled to input/output ports, and one or more memories via appropriate buses or other communication mechanisms.

The computer system 573 may also include one or more input devices (e.g., a keyboard, mouse, joystick) for providing user input, such as changing focus and other inspection recipe parameters. The computer system 573 may also be connected to the stage for controlling, for example, a sample position (e.g., focusing and scanning) and connected to other inspection system components for controlling other inspection parameters and configurations of such inspection system components.

The computer system 573 may be configured (e.g., with programming instructions) to provide a user interface (e.g., a computer screen) for displaying resultant intensity values, images, and other inspection results. The computer system 573 may be configured to analyze intensity, phase, and/or other characteristics of reflected and/or transmitted sensed light beam. The computer system 573 may be configured (e.g., with programming instructions) to provide a user interface (e.g., on a computer screen) for displaying resultant intensity values, images, and other inspection characteristics. In certain embodiments, the computer system 573 is configured to carry out inspection techniques detailed above Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of qualifying a photolithographic reticle, the method comprising:
using a reticle inspection tool, acquiring a plurality of images at different imaging configurations from each of a plurality of pattern areas of a test reticle;
recovering a reticle near field for each of the pattern areas of the test reticle based on the acquired images from each pattern area of the test reticle;
applying a lithography model to the reticle near field for the test reticle to simulate a plurality of test wafer images; and
analyzing the simulated test wafer images to determine whether the test reticle will likely result in an unstable or defective wafer.

2. The method of claim 1, further comprising:
using a reticle inspection tool, acquiring a plurality of images at different imaging configurations from each of a plurality of pattern areas of a calibration reticle;
recovering the reticle near field for each of the pattern areas of the calibration reticle based on the acquired images from each pattern area of the calibration reticle;
using the recovered reticle near field for the calibration reticle, simulating a plurality of wafer images based on the reticle near field; and
adjusting a parameter of the lithography model so that simulated wafer images agree with wafers printed using the calibration reticle.

3. The method of claim 1, wherein the lithography model is based on a recovered reticle near field from a reticle.

4. The method of claim 3, wherein the reticle near field is recovered using a quasi-Newton or conjugate gradient technique for determining the reticle near field.

5. The method of claim 3, wherein the reticle near field is recovered by a regressive technique that minimizes a sum of a plurality of squared differences between the acquired images and a plurality of images that are calculated from the reticle near field.

6. The method of claim 3, wherein the reticle near field is recovered using a Hopkins approximation.

7. The method of claim 3, wherein the reticle near field is recovered without using a design database that was used to fabricate the reticle.

8. The method of claim 3, wherein the acquired images include at least three images that are acquired at different imaging conditions selected to result in a same reticle near field.

9. The method of claim 8, wherein the different process conditions include different focus settings, different illumination directions or patterns, different linear polarization for an entire illumination pupil or different parts of an illumination pupil, and/or different apodization settings to obscure different portions of a collection beam.

10. The method of claim 1, wherein the lithography model simulates a photolithography process, including the effect of a particular photoresist material.

11. The method of claim 1, wherein the model is applied to the test reticle near field under a plurality of different lithography process conditions and analyzing the simulated test wafer images includes determining whether the test reticle will likely result in an unstable wafer under the different lithography process conditions by comparing the simulated test images having different process conditions and being associated with a same reticle area.

12. An inspection system for qualifying a photolithographic reticle, the system comprising:
a light source for generating an incident beam;
illumination optics for directing the incident beam onto a reticle;
collection optics for directing an output beam from each pattern area of the reticle to at least one sensor;
at least one sensor for detecting the output beam and generating an image or signal based on the output beam; and
a controller that is configured to perform the following operations:
causing an acquiring of a plurality of images at different imaging configurations from each of a plurality of pattern areas of a test reticle;
recovering a reticle near field for each of the pattern areas of the test reticle based on the acquired images from each pattern area of the test reticle;

applying a lithography model to the reticle near field for the test reticle to simulate a plurality of test wafer images; and analyzing the simulated test wafer images to determine whether the test reticle will likely result in an unstable or defective wafer.

13. The system of claim 12, wherein the controller is further configured for:

causing an acquiring of a plurality of images at different imaging configurations from each of a plurality of pattern areas of a calibration reticle;

recovering the reticle near field for each of the pattern areas of the calibration reticle based on the acquired images from each pattern area of the calibration reticle;

using the recovered reticle near field for the calibration reticle, simulating a plurality of wafer images based on the reticle near field; and adjusting a parameter of the lithography model so that simulated wafer images agree with wafers printed using the calibration reticle.

14. The system of claim 12, wherein the lithography model is based on a recovered reticle near field from a reticle.

15. The system of claim 14, wherein the reticle near field is recovered using a quasi-Newton or conjugate gradient technique for determining the reticle near field.

16. The system of claim 14, wherein the reticle near field is recovered by a regressive technique that minimizes a sum of a plurality of squared differences between the acquired images and a plurality of images that are calculated from the reticle near field.

17. The system of claim 14, wherein the reticle near field is recovered using a Hopkins approximation.

18. The system of claim 14, wherein the reticle near field is recovered without using a design database that was used to fabricate the reticle.

19. The system of claim 14, wherein the acquired images include at least three images that are acquired at different imaging conditions selected to result in a same reticle near field.

20. The system of claim 19, wherein the different process conditions include different focus settings, different illumination directions or patterns, different linear polarization for an entire illumination pupil or different parts of an illumination pupil, and/or different apodization settings to obscure different portions of a collection beam.

21. The system of claim 12, wherein the lithography model simulates a photolithography process, including the effect of a particular photoresist material.

22. The system of claim 12, wherein the model is applied to the test reticle near field under a plurality of different lithography process conditions and analyzing the simulated test wafer images includes determining whether the test reticle will likely result in an unstable wafer under the different lithography process conditions by comparing the simulated test images having different process conditions and being associated with a same reticle area.

* * * * *